(12) United States Patent
Buscherhoff

(10) Patent No.: US 11,134,930 B2
(45) Date of Patent: Oct. 5, 2021

(54) DEVICE FOR REMOVING ORGANS FROM A HUMAN OR ANIMAL BODY

(71) Applicants: Bernd Buscherhoff, Steinfeld (DE); Bernd Holthaus, Quernheim (DE)

(72) Inventor: Bernd Buscherhoff, Steinfeld (DE)

( * ) Notice: Subject to any disclaimer, the term of this patent is extended or adjusted under 35 U.S.C. 154(b) by 235 days.

(21) Appl. No.: 16/349,022

(22) PCT Filed: Nov. 13, 2017

(86) PCT No.: PCT/EP2017/079067
§ 371 (c)(1),
(2) Date: May 10, 2019

(87) PCT Pub. No.: WO2018/087368
PCT Pub. Date: May 17, 2018

(65) Prior Publication Data
US 2019/0261968 A1    Aug. 29, 2019

(30) Foreign Application Priority Data
Nov. 11, 2016 (DE) .......................... 202016006899.8

(51) Int. Cl.
*A61B 17/22* (2006.01)
*A61B 17/3207* (2006.01)
(Continued)

(52) U.S. Cl.
CPC .. *A61B 17/00234* (2013.01); *A61B 17/22032* (2013.01); *A61B 17/320758* (2013.01);
(Continued)

(58) Field of Classification Search
CPC ..... A61B 17/22; A61B 17/3205; A61B 17/50; A61B 2017/00287; A61B 2017/00358;
(Continued)

(56) References Cited

U.S. PATENT DOCUMENTS

| 5,215,521 A | 6/1993 | Cochran et al. |
| 5,779,716 A * | 7/1998 | Cano ...................... A01N 59/00 606/110 |

(Continued)

FOREIGN PATENT DOCUMENTS

| EP | 2211972 | 8/2010 |
| EP | 2470088 | 7/2012 |

(Continued)

OTHER PUBLICATIONS

International Search Report and Written Opinion from PCT/EP2017/079067 dated Dec. 22, 2017, 14 pages.

(Continued)

*Primary Examiner* — Ryan J. Severson
(74) *Attorney, Agent, or Firm* — Mueting Raasch Group

(57) ABSTRACT

A device for removing organs from a human or animal body has a tube, said device comprising a proximal and a distal end where the proximal end is provided for partly introducing into the body, and whereby the distal end of the tube is connectable to a suction air source and the proximal end of the tube is designed to come into suction contact with the organ. The device also comprises a tubular casing, which surrounds some sections of the tube, and has a proximal end and a distal end that is connected to the tube; a handling device arranged on the tube and designed to open or expand the proximal end of the tubular casing and to guide or place it around the organ; a closing device to close the proximal end of the tubular casing, and a comminuting device provided in the tube.

37 Claims, 12 Drawing Sheets

(51) Int. Cl.
  *A61B 17/00* (2006.01)
  *A61B 17/34* (2006.01)
  *A61B 17/30* (2006.01)
  *A61B 17/3205* (2006.01)

(52) U.S. Cl.
  CPC ....... *A61B 17/3205* (2013.01); *A61B 17/3423* (2013.01); *A61B 2017/00287* (2013.01); *A61B 2017/00353* (2013.01); *A61B 2017/00566* (2013.01); *A61B 2017/306* (2013.01); *A61B 2217/005* (2013.01)

(58) Field of Classification Search
  CPC .... A61B 2017/008; A61B 2017/00823; A61B 2017/22079; A61B 2017/306; A61B 2017/3425
  See application file for complete search history.

(56) References Cited

U.S. PATENT DOCUMENTS

| | | | |
|---|---|---|---|
| 5,836,953 A | 11/1998 | Yoon | |
| 6,156,055 A * | 12/2000 | Ravenscroft | A61F 2/01 606/206 |
| 6,168,604 B1 * | 1/2001 | Cano | A01N 59/00 606/110 |
| 6,280,450 B1 * | 8/2001 | McGuckin, Jr. | A61B 17/221 606/114 |
| 7,044,956 B2 * | 5/2006 | Vetter | A61B 10/0266 606/167 |
| 7,122,011 B2 * | 10/2006 | Clifford | A61B 10/0266 600/564 |
| 8,172,772 B2 * | 5/2012 | Zwolinski | A61B 10/06 600/562 |
| 8,348,827 B2 * | 1/2013 | Zwolinski | A61B 17/00234 600/104 |
| 8,900,257 B2 | 12/2014 | Straub et al. | |
| 8,945,141 B2 * | 2/2015 | Cahill | A61B 17/3439 606/108 |
| 9,463,035 B1 * | 10/2016 | Greenhalgh | A61B 17/22 |
| 9,603,586 B2 * | 3/2017 | Vetter | A61B 10/0266 |
| 9,717,515 B1 * | 8/2017 | McCarty | A61B 17/221 |
| 9,770,252 B2 * | 9/2017 | Smith | A61B 17/221 |
| 9,832,980 B2 * | 12/2017 | Kovarik | E01H 1/1206 |
| 9,987,031 B2 * | 6/2018 | Menn | A61B 17/00234 |
| 10,092,324 B2 * | 10/2018 | Gillespie | A61B 17/22031 |
| 10,226,266 B2 * | 3/2019 | Kovarik | A61B 17/00234 |
| 10,548,611 B2 * | 2/2020 | Ibrahim | A61B 17/52 |
| 10,813,663 B2 | 10/2020 | Bruzzi et al. | |
| 10,849,604 B2 * | 12/2020 | Yang | A61B 17/3474 |
| 2004/0242960 A1 | 12/2004 | Orban | |
| 2008/0249558 A1 * | 10/2008 | Cahill | A61B 17/50 606/198 |
| 2012/0130392 A1 * | 5/2012 | Levy | A61B 17/320016 606/114 |
| 2015/0305757 A1 * | 10/2015 | Brayman | A61B 17/221 606/128 |
| 2016/0242788 A1 * | 8/2016 | Ibrahim | A61B 17/50 |
| 2016/0262763 A1 * | 9/2016 | Shankarsetty | A61B 17/1285 |
| 2017/0119410 A1 * | 5/2017 | MacTaggart | A61B 17/221 |
| 2018/0193050 A1 * | 7/2018 | Hawkins | A61B 17/12013 |
| 2019/0209148 A1 * | 7/2019 | Yang | A61B 17/29 |
| 2019/0261968 A1 * | 8/2019 | Buscherhoff | A61B 17/22032 |

FOREIGN PATENT DOCUMENTS

| | | |
|---|---|---|
| EP | 2967614 | 1/2016 |
| WO | 2004002334 | 1/2004 |
| WO | 2011157338 | 12/2011 |
| WO | 2015118542 | 8/2015 |

OTHER PUBLICATIONS

Office Action from Indian Application No. 201947022445 dated Jul. 22, 2021, 5 pages.

* cited by examiner

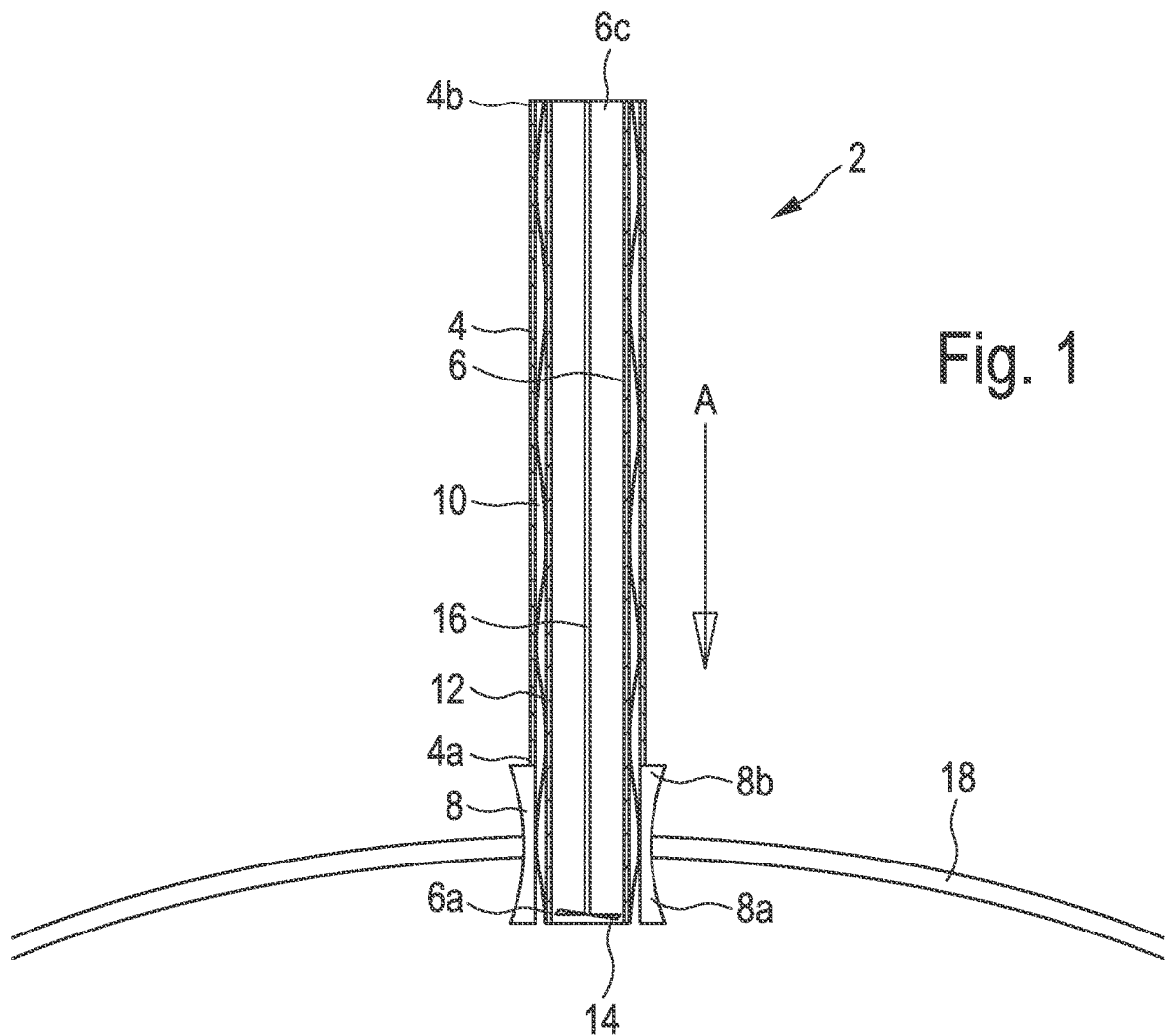
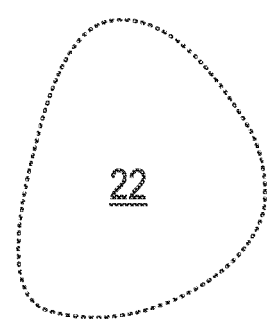

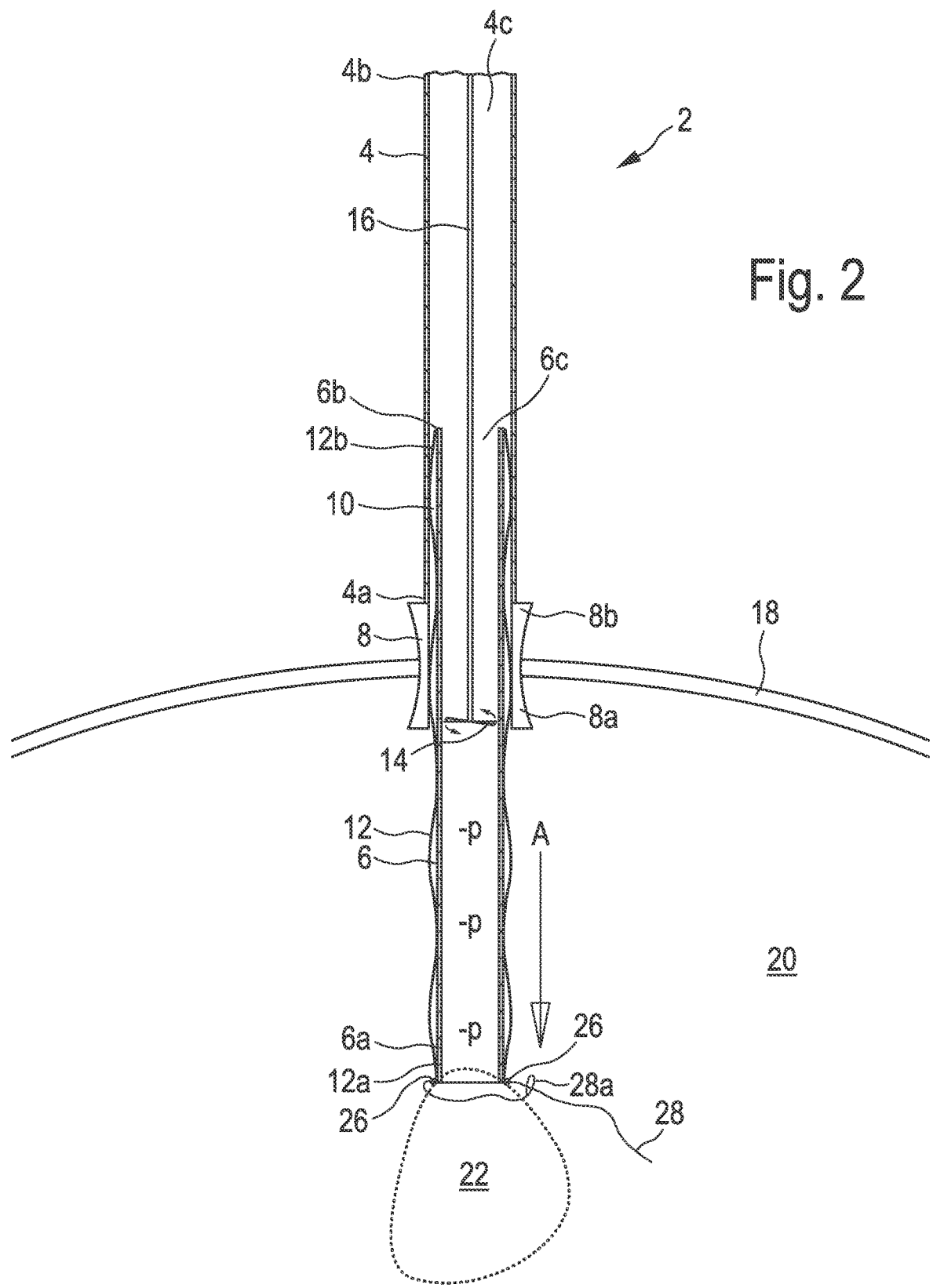

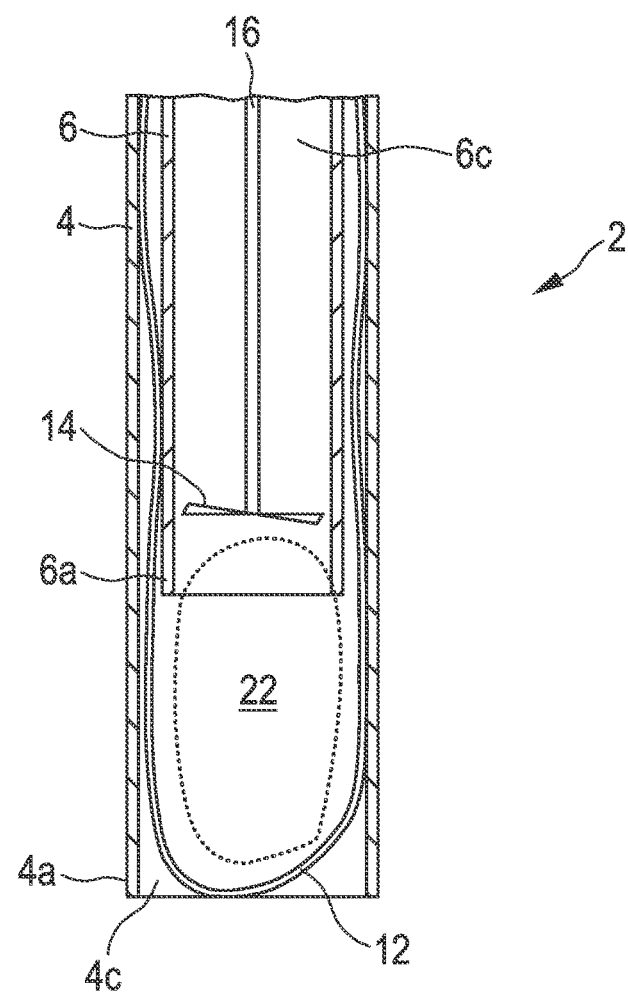
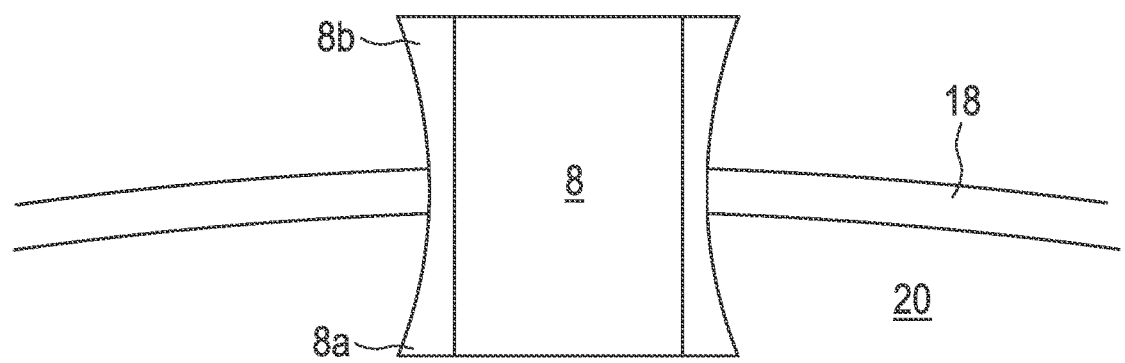
Fig. 8

DEVICE FOR REMOVING ORGANS FROM A HUMAN OR ANIMAL BODY

The invention relates to a device for removing organs from a human or animal body.

A device of this type serves in the removal of inner organs that have suffered in particular as a result of diseases or other negative effects and can no longer properly perform their function or have suffered necrosis. In particular, a device of this nature is intended to remove a pathological uterus. Many of the devices of the above-mentioned type work in an endoscopic manner and comprise at least two endoscopes, one of which comprises forceps to sever the organ to be removed. However, when using these prior-art devices, it was not possible, or required extreme effort, to create sterile surroundings in the body in the area of the organ to be removed, so that remnants and residual particles of the removed organ remained in the body, which led to an undesired contamination within the body. The problem with these prior-art devices in particular results from the severed organ falling into the body section below it due to gravity, which not only favours contamination but also leads to sterility problems.

One objective of the present invention is to present an improved device of the above-mentioned type that aids in easily creating a substantially sterile environment within the body in the area of the organ to be removed and further makes it possible to substantially prevent a contamination with remnants and residual particles of the removed organ.

This objective is met by the invention with a device for removing organs from the human or animal body, with a tube that comprises a proximal end and a distal end and is intended to be partially introduced into the body with its proximal end, whereby the distal end of the tube can be connected to a suction air source and the proximal end of the tube is embodied for a suctional engagement with the organ to be removed, said device comprising a tubular casing at least sectionally enclosing the tube that possesses a proximal end and a distal end, by which it is attached to the tube, further comprising a handling device, which preferably is arranged and embodied at the tube, in order to open or extend the tubular casing at its proximal end, to guide or place it around the organ, and comprising a closing device, which is embodied to close the proximal end of the tubular casing, and a comminuting device, which is provided within the tube, preferably in the area of its proximal end.

The invention's use of a tubular casing, which at its proximal end is at first opened or extended, subsequently is guided or placed around the organ, and finally is closed at its proximal end, makes it possible to securely and completely enclose the organ to be removed in a simple manner, which to the highest degree possible achieves the required sterility and at the same time prevents contamination with remnants or residual particles of the organ to be removed. According to the invention, this is achieved with a handling device, which is arranged and embodied at a tube to be inserted into the body, and is designed to open or extend the tubular casing at its proximal end, to guide or place the tubular casing around the organ, and with a closing device that is embodied to close the proximal end of the tubular casing. The term "arranged at the tube" may also refer to a position of the handling device along the tube and/or adjacent to the tube, as well as an arrangement without being attached to the tube. After closing the proximal end of the tubular casing by means of the closing device, the tubular casing assumes the shape of a pouch, which now accommodates the organ to be removed.

The invention also provides a simple but effective solution for the removal of the organ to be eliminated from the body, which meets the stringent requirements for necessary sterility. In this regard, the invention intends that the distal end of the tube can be connected to a suction air source and the proximal end of the tube is embodied for a suction engagement with the organ to be removed, as a result of which the organ to be removed, which is entrapped in a bag-like manner by the tubular casing connected to the tube's proximal end and is consequently separated from the surroundings, i.e. the rest of the body, is sucked into the proximal end of the tube. The invention further provides a comminuting device, which is arranged and embodied within the tube in the area of its proximal end, for the purpose of comminuting the organ to be removed, while it is drawn into the proximal end of the tube by the suction air source. The comminuting reduces the volume of the organ to be removed and consequently also the volume of the closed tubular casing that accommodates the organ in the way of a pouch, which improves the ease with which the organ to be removed can be withdrawn through the tube.

At this point it should be mentioned that the term "proximal", which according to the German Duden dictionary means "closer to the centre of the body" and the term "distal", which according to the German Duden dictionary means "further from the center of the body", in the present context refer to the position relative to the organ to be removed within the body prior to the organ's removal.

Preferred embodiments and further developments of the invention are described in the dependent claims.

Consequently it is practical to arrange the handling device relative to the tube moveable along the latter's longitudinal direction between an extended proximal final position and a retracted distal final position, whereby in a preferred further development, the handling device is also arranged moveable along the transverse direction of the tube, in order to effectively place the tubular casing around the organ in dependence on the respective position of the organ to be removed.

A particularly preferred design of the handling device is characterized in that it comprises opposingly situated gripping arms, each of which possesses a proximal end and a distal end, and which are embodied to releasably grip the tubular casing, preferably in the region of the latter's proximal end.

Advantageously, the gripping arms comprise, preferably in the region of their proximal ends, securing means that are embodied to detachably secure the tubular casing, preferably at its proximal end, to the gripping arms.

Expediently, the gripping arms are aligned along the longitudinal direction of the tube.

Preferentially, the gripping arms are embodied to be elastic and are arranged at an angle, preferably for example transversely, to the longitudinal extent of the tube. In a preferred further development, in the relaxed state of the gripping arms, the proximal ends of the respectively opposing gripping arms are separated by a distance that is less than the diameter of the tube, and a central section of the gripping arms, situated between the proximal and the distal ends, is curved outward with respect to the tube, so that at least at the location that is furthest outward along the radial direction, the distance of the central sections to respective opposing gripping arms is greater than the distance between the proximal ends of said gripping arms, and preferably also greater than the diameter of the tube. Such a shape of the gripping arms is particularly advantageous, not only to guide or place the tubular casing around the organ, but also to securely hold the organ enclosed by the closed tubular casing in the region of the central sections of the gripping arms. Further, the elasticity in combination with the shape also ensures that the gripping arms are at first opened at their proximal end against the force exerted by the elasticity, which results in an opening or widening of the tubular casing at its proximal end, and that subsequently the pretension generated by the elasticity is used to bring the proximal ends of the gripping arms back to their closed position after the organ has been enclosed.

In a further preferred embodiment, the exterior side of the tube is equipped along its longitudinal direction with guide grooves, in which the gripping arms are accommodated moveable along the grooves' longitudinal direction, and the arrangement is designed so that in the proximal final position of the handling device, the gripping arms extend beyond the proximal end of the tube with a portion connected to their proximal ends and thus are exposed. This facilitates an especially large range of motion for the gripping arms.

The handling device preferably comprises spreading elements, which are embodied so that they at least partially spread apart the gripping arms to their proximal final position during the movement of the handling device, in order to open or extend the tubular casing at its proximal end and to guide or place it around the organ.

In a preferred further development of this embodiment, the spreading elements are arranged at the tube in the area of its proximal end and possess a guide surface, which rises between the exterior side of the tube and the latter's proximal end, and to which the gripping arms may be brought in contact with. Thus the radial distance of the guide surfaces of the spreading elements at their proximal ends or at the proximal end of the tube is greater than the tube radius, and consequently the radial separation between the guide surfaces of opposing spreading elements at their proximal ends or at the proximal end of the tube is greater than the tube diameter. Consequently, the spreading elements of this preferred further development act in a cone-like manner to spread the gripping arms in contact with them. If guide grooves extending along the longitudinal direction are embodied on or in the exterior side of the tube, the spreading elements may preferentially be arranged in these guide grooves and their guide surfaces may rise from the bottom of the guide grooves.

In a preferred further development, the spreading elements are arranged separated by some distance, one spreading element is associated with each gripping arm, and for the purpose of releasing the gripping arms from the spreading elements, the tube on the one hand and/or the gripping arms on the other hand can be subjected to a relative motion with respect to each other, in order to deliver the gripping arms into a position laterally next to the spreading elements. Thus, a lateral displacement of the tube relative to the gripping arms or a lateral displacement of the gripping arms relative to the tube or a corresponding joint lateral displacement of the tube and the gripping arms relative to each other causes the gripping arms to slide off the spreading elements, and thus the closing of the gripping arms.

Preferably the gripping arms are connected to each other in the area of their distal ends, which simplifies the handling of the gripping arms, in particular during their movement into the proximal end position. An advantageous further development comprises an annular element, to which the gripping arms are mounted at their distal end, and which preferably can be used as a handling element.

The closing device expediently is provided at the handling device. If gripping arms are employed, then the closing device preferably comprises closing means, which are provided at the gripping arms, preferably at their exposed i.e. proximal ends. Further, the closing device can preferably comprise eyes or eyelets provided at the proximal end of the tubular casing as well as at least one thread or wire that can be threaded through the eyes or eyelets, as a result of which the closing process of the proximal end of the tubular casing takes place in the manner of a sewing process.

To provide for a particularly effective comminuting of the organ to be removed, the comminuting device preferably comprises at least one rotatably supported cutting blade.

A sleeve preferably is provided to be arranged on the body surface or to be inserted into the body surface, whereby the tube extends through the sleeve and is moveable relative to the sleeve. A sleeve of this type facilitates fixing the device in position on the surface of the body and also allows a simpler and more accurate alignment of the tube when the latter is inserted into the body in the direction of the organ to be removed.

If gripping arms are included, the gripping arms preferentially are arranged between the inner side of the sleeve and the exterior side of the tube, and are in contact with the inner side of the sleeve and the exterior side of the tube. An arrangement of this type facilitates a reliable guiding of the gripping arms. If the gripping arms are embodied with a central section with an outwardly curved shape that is located between the proximal and the distal ends, then this arrangement results in a spreading due to the curved shape of the gripping arms. In the retracted distal final position of the handling device, in which the gripping arms are in their so-called starting position, the gripping arms are forced by the sleeve into a substantially completely extended state and consequently are substantially completely stretched, since the interspace between the exterior side of the tube and the inner side of the sleeve does not provide any substantial room for movement; consequently this state can also be referred to as a forced constraint, which arises out of the mentioned configuration and does not provide the gripping arms with any other choice but to assume a completely extended shape. When the handling device is moved in the direction towards its proximal final position, and the gripping arms correspondingly are extended, then the curved shape of the central section of the gripping arms at first causes the gripping arms to spread apart, at least for as long as the curved shape of the outwardly curved central section of the gripping arms contributes to generating a force that pushes the central section of the gripping arms outward towards the inner side of the sleeve, and subsequently a closing of the gripping arms again, no later than when the outwardly curved central section of the gripping arms is exposed outside of the sleeve and thus when the gripping arms no longer are subject to any force effects from the sleeve.

In a preferred further development, the inner side of the sleeve is equipped with guide grooves, which extend along the direction of movement of the handling device, and in which the gripping arms are arranged moveable along the grooves' longitudinal direction, and the arrangement is designed so that in the proximal final position of the handling device, the gripping arms with their section adjoining to their proximal end project beyond the proximal end of the tube and consequently are exposed.

The sleeve preferably possesses a flange-like rim to facilitate a reliable bearing contact on the surface of the body.

In a further preferred embodiment, the tubular casing is embodied as a double casing with an inner casing and an outer casing, which surrounds the inner casing at a distance while forming an interspace, and a pressurized air source can be connected to the interspace formed between the inner casing and the outer casing. Connecting a pressurized air source facilitates inflating and pressurizing the interspace between the inner casing and the outer casing. This has three effects. A larger space is created around the organ to be removed, which facilitates the handling of the device and in particular that of the handling device. Furthermore, the in-body surroundings of the organ to be removed are being stabilized. Finally, and this is a very important aspect, the organ to be removed is pressurized, which effects a compression of the organ, which in turn, acting in addition to the underpressure prevalent there due to the suction action, speed up and thus promotes the removal of the organ through the tube.

In this embodiment, the closing device may be embodied for closing the proximal end of the inner casing and for closing the proximal end of the outer casing or alternatively for jointly closing the proximal ends of the inner casing and the outer casing.

In a further preferred further development of this embodiment, the handling device is at least partially arranged in the interspace formed between the inner casing and the outer casing. This prevents the organ to be removed from coming into contact with the handling device and ensures a reliable handling of the tubular casing for enclosing the organ.

In a further preferred further development of this embodiment the inner casing is connected in a sealing manner to the outer casing at the proximal end of the tubular casing. This further development is particularly advantageous since the closing device has to close the common proximal end of the tubular casing formed by the inner casing and the outer casing in a single operating cycle. A further advantage is realized if at least some sections of the handling device are arranged in the interspace between the inner casing and the outer casing, because the handling device with its proximal end comes into bearing contact from the inside to the proximal end of the tubular casing that connects the inner casing with the outer casing in a sealing manner and consequently the tubular casing can be particularly easily handled with the help of the handling device. This in particular applies when gripping arms are employed, over which the tubular casing embodied as a double casing can be pulled in the manner of a sock.

In a further particularly preferred embodiment, the tube is embodied as in inner tube, which is encompassed by an outer tube with an interspace formed between them; the inner tube is arranged moveable relative to the outer tube, and in this is arranged so that the section adjacent to its proximal end can be extended from the proximal end of the outer tube; the tubular casing prior to its use is substantially arranged in the interspace between the inner tube and the outer tube and can be exposed by extracting the inner tube from the outer tube; and the comminuting device is provided in the inner tube in the area of the latter's proximal end. Consequently this embodiment of the invention facilitates 'hiding' the tubular casing prior to its deployment in the interspace between the inner tube and the outer tube, so that it only is deployed after the device has been introduced into the body by pulling the inner tube from the outer tube.

When using the above-mentioned sleeve, the sleeve preferably is arranged at the proximal end of the outer tube or is even formed by the outer tube itself.

Furthermore, the handling device can be arranged and embodied either at the exterior side of the inner tube or at the outer tube, in dependence on the space requirements of the device.

Expediently, the tubular casing should be attached by its distal end to the inner tube, since the disposal of the organ to be removed takes place through the inner tube.

Prior to deployment of the device, the inner tube usually is retracted in the outer tube and the handling device is also in a retracted position, in which it at least does not protrude beyond the outer tube and the inner tube. During the extraction of the inner tube from the outer tube, preferably at first the handling device is taken along by the inner tube or the handling device is moved substantially in parallel to the inner tube, whereby the handling device takes along the tubular casing and pulls at least the greater portion of the latter from the interspace originally formed between the inner tube and the outer tube and thus removes it from the outer tube, until the proximal end of the inner tube is situated in proximity to the organ to be removed or even has come into contact with the latter. Preferably, the handling device is subsequently moved relative to the inner tube, in order to open or extend the proximal end of the tubular casing taken along by the handling device, and to guide or place it around the organ to be removed. Alternatively or supplementary it can also be envisioned that in a further development of the above-mentioned embodiment the inner tube is embodied in a way so that during its extraction from the outer tube it takes along the tubular casing and substantially exposes the latter.

If the tubular casing is embodied as a double casing, the inner casing preferably can be fastened to the inner tube while the outer casing is fastened to the outer tube, and the pressurized air source can be connected to the interspace formed between the inner tube and the outer tube. Thus, not only is it particularly simple and simultaneously reliable to connect the pressurized air source to the device outside of the body, but the pressurized air is also delivered in a simple yet effective manner into the tubular casing, which is embodied as a double casing, inside the body.

Preferred embodiment examples are explained in the following with the help of the figures. The figures show:

FIG. 1 shows a schematic longitudinal sectional view of a device to remove organs from the human or animal body in accordance with a first preferred embodiment in an initial first operating state;

FIG. 2 shows a schematic longitudinal sectional view of the device of FIG. 1 in a second operating state, in which the device is already in contact with the organ to be removed;

FIG. 8 shows a schematic longitudinal sectional view of the device of FIG. 1 in an eighth operating state where it is substantially completely removed from the body;

Figure 12:
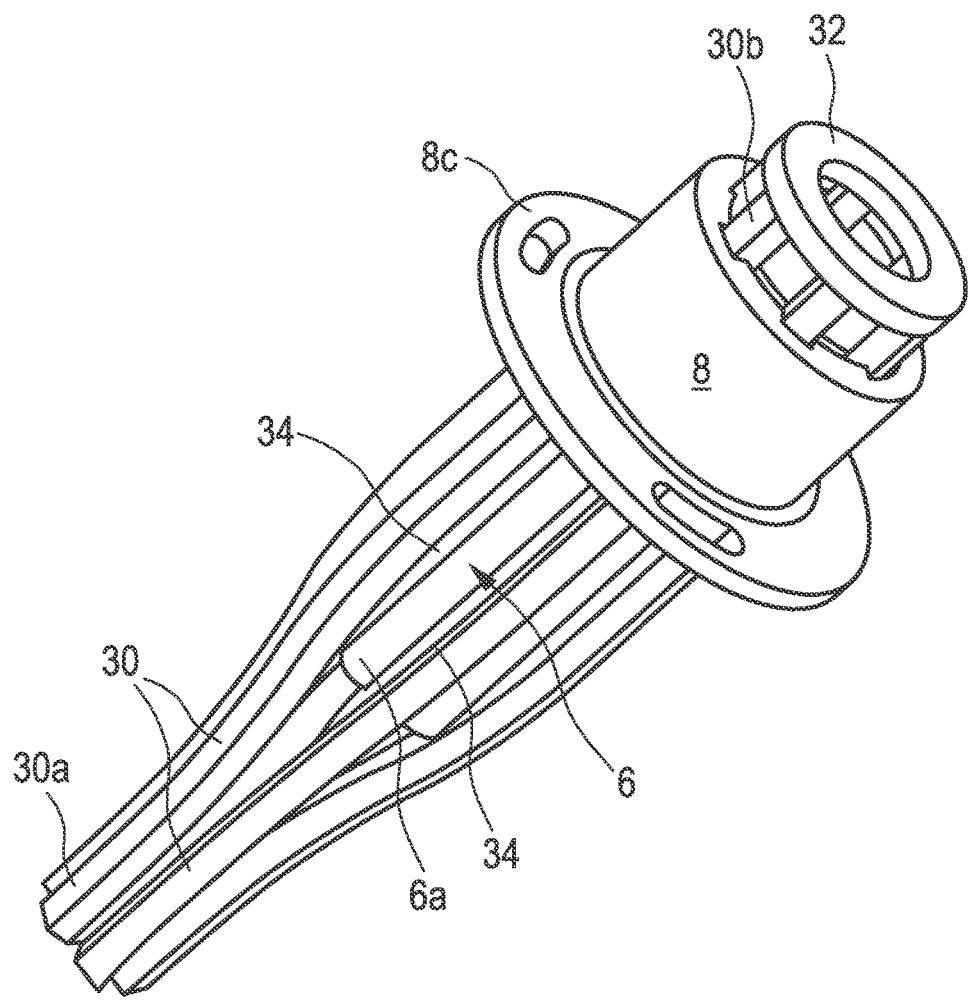
FIG. 12 shows in a schematic perspective view at least part of a handling device with gripping arms as part of a device for removing organs from the body of human or animal, in accordance with a third preferred embodiment.
Figure 13:
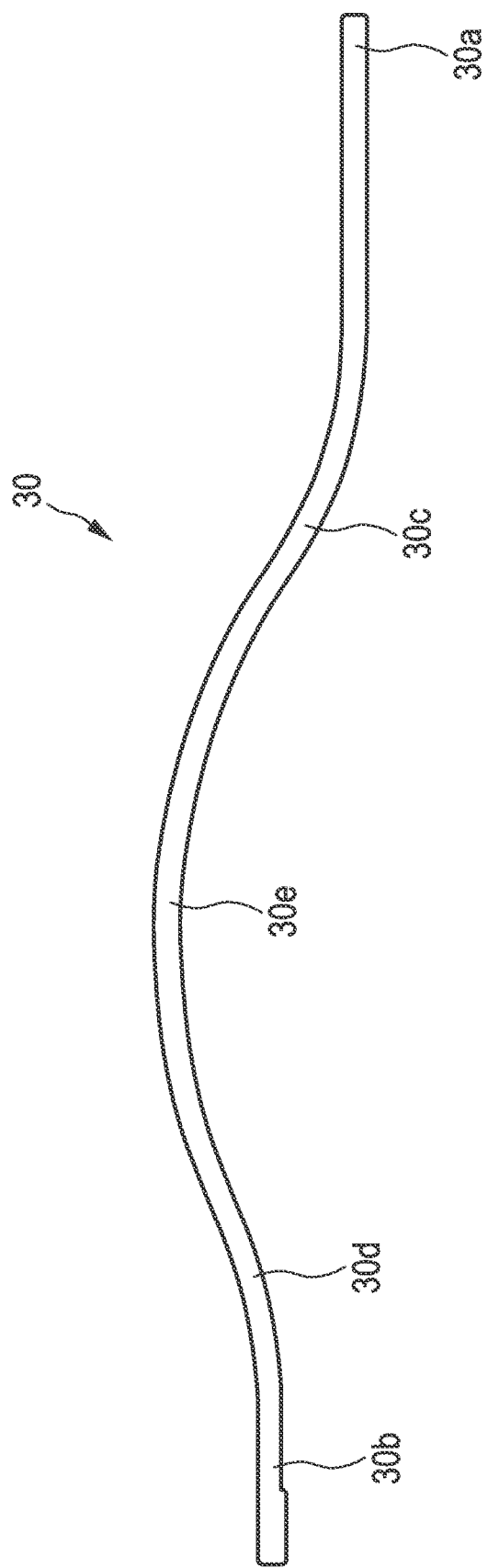
Figure 14:
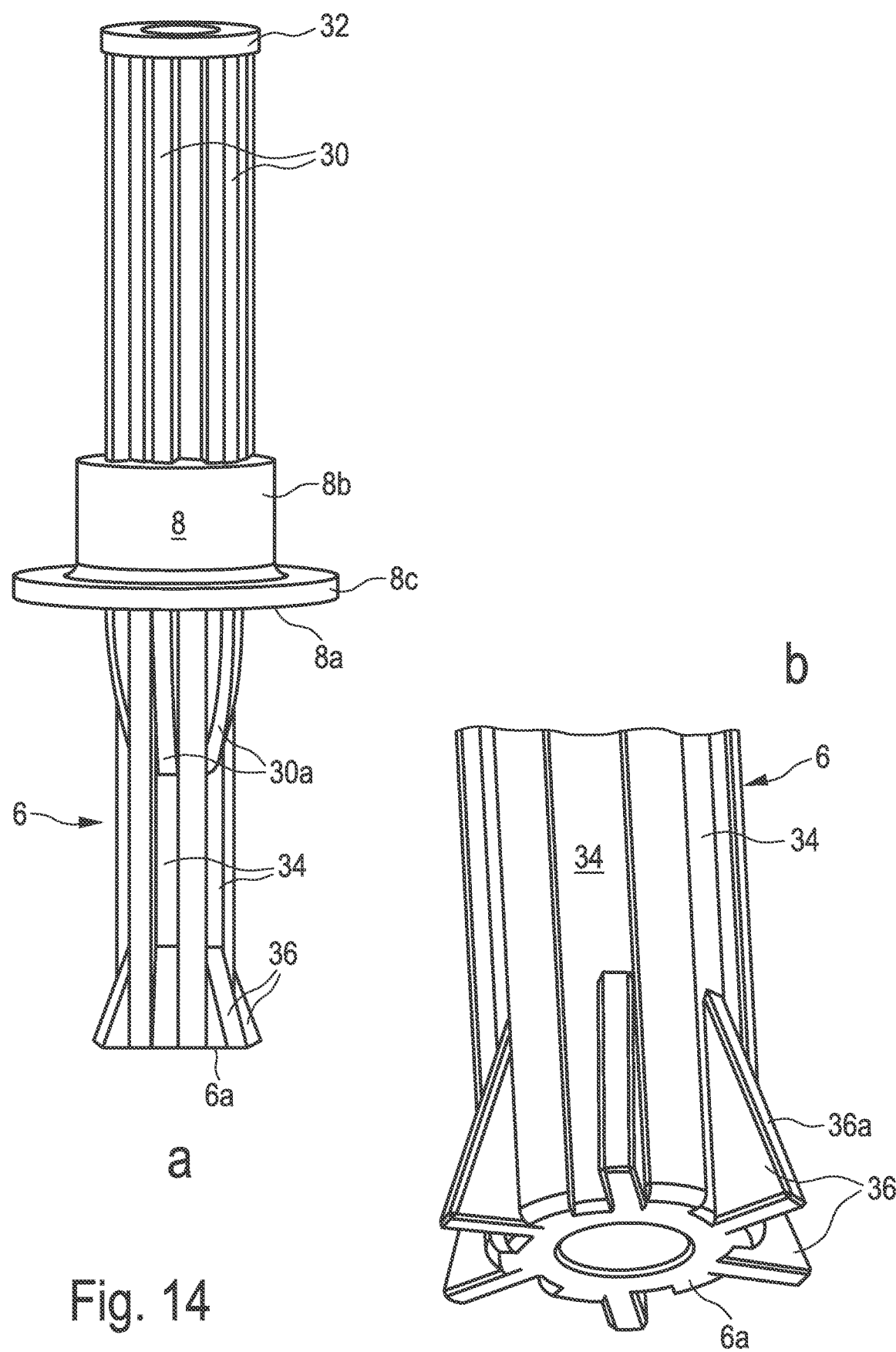

FIG. 13 shows a lateral view of the shape of a gripping arm of the first embodiment of FIG. 12; and FIG. 14 shows a schematic perspective lateral view of at least part of a handling device with gripping arms as part of a device in accordance with a fourth preferred embodiment, whereby FIG. 14a shows the handling device according to the second embodiment in its entirety, and FIG. 14b shows a section in the area of the proximal end of an inner tube.

FIG. 1 shows in a schematic longitudinal sectional view a device 2 for removing organs from the human or animal body according to a first preferred embodiment example, in an initial first operating state.

The device 2 comprises an outer tube 4 with an open proximal end 4a and an open distal end 4b, as well as an inner tube 6 with an open proximal end 6a and an open distal end 6b. In the shown embodiment example, the device 2 further comprises a sleeve 8, which comprises an open proximal end 8a and an open distal end 8b, and which forms an extension of the outer tube 4, since the outer tube 4 with its proximal end 4a is attached to the distal end 8b of the sleeve 8. Relative to the arrangement of outer tube 4 and sleeve 8, the inner tube 6 is supported moveable along the arrangement's longitudinal direction, for which purpose corresponding suitable support or guide elements must be provided, which however are not shown in the figures. Between the inner side of the outer tube 4 and the sleeve 8 on the one hand and the exterior side of the inner tube 6 on the other extends an interspace with an annular cross-section, which in the initial first operating state shown in FIG. 1 accommodates a tubular casing 12. In the shown embodiment example, the device 2 further comprises a comminuting device, which comprises a blade, which is arranged in the area of the proximal end 8a of the sleeve 8, and which in the shown embodiment example is embodied as a rotary blade arranged rotatable about the longitudinal axis of the inner tube 6, and said blade is situated at the end of a rotating shaft 16, the rotational axis of which coincides with the longitudinal axis of the inner tube 6, and which is set in rotation by a motor that is not shown. As is further evident in FIG. 1, the outer tube 4, the inner tube 6, and the sleeve 8 in the shown embodiment example are arranged substantially concentrically relative to each other, so that their longitudinal axes substantially coincide.

The sleeve 8 aids in the insertion of the device 2 into the skin 18 of the human or animal body 20 and simultaneously for securing the device 2 in the direction to an organ 22 to be removed from the body 20, as is also evident in FIG. 1. In this, in the initial first operating state shown in FIG. 1, the device 2 is already arranged on the skin 18 of the body 20 or is inserted into the skin 18 of the body 20 with the help of the sleeve 8, but otherwise is not yet in a functional operating state.

FIG. 2 shows the device 2 in a second operating state. In this state, the inner tube 6 has been moved relative to the outer tube 4 and the sleeve 8 along the direction of arrow A, whereby the tube 6 has been pulled out of the proximal end 8a of the sleeve 8 and has been inserted more deeply into the body 20 in the direction of the organ 22 to be removed, until the proximal end 6a of the inner tube 6 comes in contact with the organ 22 to be removed. However, the inner tube 6 with its distal end 6b and a section connected thereto continues to remain within the outer tube 4 and the sleeve 8, while the inner tube 6 with its remaining section, adjacent to the proximal end 6a, extends out of the sleeve 8 into the body 20 and consequently this section is exposed within the body 20. The same applies to the tubular casing 12, which during the movement out of the outer tube 4 and the sleeve 8 is taken along by the inner tube 6, so that with its distal end 12b it is still situated within the remaining interspace 10 between the outer tube 4 and the sleeve 8 on the one hand and the inner tube 6 in the section adjacent to the distal end 6b of the inner tube 6 on the other hand, but with all other parts is exposed and its proximal end 12a, which was taken along by the inner tube 6 during the latter's movement, is situated next to the organ 22. Connected to the open distal end 4b of the outer tube 4 is a negative pressure device, i.e. a suction device, which is not shown in the figures, for the purpose of generating an underpressure, which in FIG. 2 is schematically referenced as '-p', in the cavity 4c of the outer tube 4b and in the cavity 6c of the of the inner tube 6, which communicates with the cavity 4c of the outer tube 4 via the open distal end 6b of the inner tube 6. The underpressure within the cavity 6c of the inner tube 6 gives rise to a suction effect at the proximal end 6a of the inner tube 6, as a result of which the organ 22 is drawn into the proximal end 6a of the inner tube 6. In this manner, an initially loose contact between the proximal end 6a of the inner tube 6 and the organ 22 to be removed changes to the organ 22 being secured in position at the proximal end 6a of the inner tube 6.

As is further indicated schematically in FIG. 2, in the illustrated embodiment example eyelets 26 are fastened at the proximal end 12a of the tubular casing 12, through which can be threaded a wire or thread 28, which at its end is provided with a loop 28a. FIG. 2 shows the thread 28 in a state, in which it has already been threaded through the eyelet 26 and the loop 28a. The thread 28 usually is already suitably prepared prior to the use of the device, i.e. it has been threaded or guided in a loose state through the eyelet 26 at the proximal end 12a of the tubular casing 12, and through the loop 28a provided at one of its own ends. Therefore in the initial first operating state of FIG. 1, the thread 28 together with the eyelets 26 and the loop 28a are situated in the interspace 10 between the outer tube 4 and the sleeve 8 on the one side and the inner tube 6 on the other side, and in particular usually in the region of the proximal end 4a of the outer tube 4 or the sleeve 8, which however is not shown in FIG. 1. In the second operating state of the device 2 of FIG. 2, and thus in the extended state of the inner tube 6, the operation of the thread 28, which in the following will be explained in more detail, can be performed in various manners. For example, the thread 28 may be guided along the inner tube 6, through the interspace 10 remaining between the outer tube 4 and the sleeve 8 on the one side and the section of the inner tube 6 adjoining the distal end 6b of the inner tube 6 on the other side, and subsequently to the outside via the cavity 4c of the outer tube 4, from where it can be controlled. But alternatively it can also be envisioned to control the thread 28 with the help of an endoscope, which is not shown in the figures, and which preferably is inserted into the body 20 via an existing body orifice. Moreover, instead of the above-mentioned pre-assembled threading it is at least theoretically also possible to guide the thread 28 through the eyelets 26 and the loop 28a only subsequently, within the body 20, which then generally can only be carried out with the help of an endoscope not shown in the figures.

Also, for completeness sake it should be noted at this point that the organ 22 to be removed should be separated and thus detached from its surroundings in the body 20 no later than when the device 2 reaches its second operating state illustrated in FIG. 2, for which one preferably also uses an endoscope with a cutting blade, which is also not shown in the figures.

Figure 3:
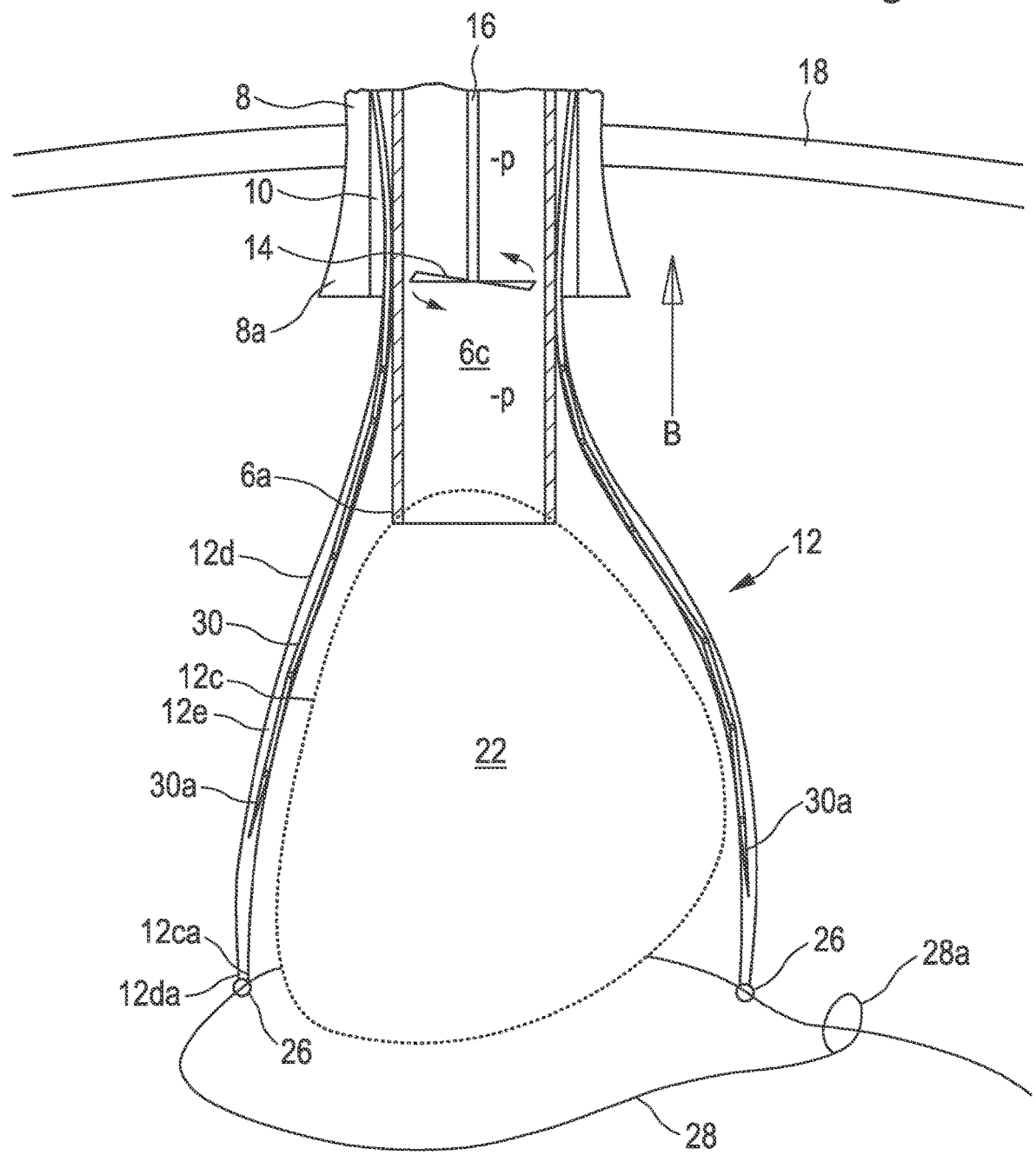
FIG. 3 shows in a schematic longitudinal sectional view an enlarged partial view of the device of FIG. 1 in a third operating state.

FIG. 3 illustrates further details of the device 2 of the first embodiment. The tubular casing 12 is embodied as a double casing with an inner casing 12c and an outer casing 12d, whereby an interspace 12e is formed between the inner casing 12c and the outer casing 12d. In the operating states that are shown in FIGS. 1 to 3, the tubular casing 12 is open at its proximal end 12a. The interspace 12e between the inner casing 12c and the outer casing 12d at the proximal end 12a of the tubular casing 12 is closed by connecting the proximal end 12ca of the inner casing 12c and the proximal end 12da of the outer casing 12d to each other via the entire circumference of the proximal end 12a of the tubular casing 12.

Furthermore, FIG. 3 indicates as a further component of the device 2 at least part of a handling device in the form of gripping arms 30, which in the illustrated embodiment example have an elongated rod shape and are aligned along the longitudinal extent of the inner tube 6. The gripping arms 30 are arranged within the interspace 10. Moreover, the gripping arms 30 are moveable both along the direction of their longitudinal extent and relative to the outer tube 4 and the sleeve 8 on the one hand and the inner tube 6 on the other hand, for which purpose the handling device comprises corresponding suitable supporting and guiding means, which however are not shown in the figures, as well as actuators and/or handling or driving means, which also are not shown in the figures. Preferably the gripping arms 30 are supported at the exterior side of the inner tube 6, moveable along the latter's longitudinal direction, so that during the extending of the inner tube 6 from the sleeve 8, during the transition from the initial first operating state of the device 2 in accordance with FIG. 1 into the second operating state of the device 2 in accordance with FIG. 2, the gripping arms 30 are at least initially taken along by the inner tube 6. But alternatively it can on principle also be envisioned that the gripping arms 30 are supported at the inner side of the outer tube 4 to be moveable along the latter's longitudinal direction. In the initial first operating state of the device 2, the gripping arms 30 are also accommodated within the interspace between the outer tube 4 and the sleeve 8 on the one side and the inner tube 6 on the other hand, which however is not discernible in FIGS. 1 and 2.

It is further evident in FIG. 3 that the gripping arms 30 are arranged at least with the section adjacent to their proximal end 30 between the inner casing 12c and the outer casing 12, and consequently within the interspace 12e formed between the inner casing 12c and the outer casing 12d within the tubular casing 12, so that—to express it differently—the tubular casing 12 embodied as a double casing accommodates the gripping arms 30 in the manner of a sock. For this purpose, the inner casing 12c is fastened to the exterior side of the inner tube 6, preferably in the area of its proximal end 6a, and the outer casing 12d is fastened to the inner side of the sleeve 8 or of the outer tube 4, so that the interspace 10 formed between the outer tube 4 and the sleeve 8 on the one hand and the inner tube 6 on the other hand communicates with the interspace 12e formed between the inner casing 12c and the outer casing 12d. Such an arrangement ensures in this embodiment that the tubular casing 12 is guided by the gripping arms 30, and not only during the emergence from the interspace 10 between the outer tube 4 and the sleeve 8 on the one hand and the inner tube 6 on the hand, during the extending movement of the inner tube 6 out of the sleeve 8 in the direction of the arrow A shown in FIGS. 1 and 2, but also for a relative movement of the tubular casing 12 relative to the inner tube 6, in particular to guide the tubular casing 12 beyond the proximal end 6a of the inner tube 6 out into the direction of the organ 22 to be removed, in particular also substantially in the direction of the arrow A shown in FIGS. 1 and 2.

The gripping arms 30 are not only moveable along their longitudinal direction, but, as is also indicated in FIG. 3, in the transverse direction, i.e. they can spread. As is also evident in FIG. 3, the organ 22 to be removed is usually wider than the diameter of the inner tube 6. Consequently one requires also an outwardly directed spreading movement of the gripping arms 30, in order to be able to—during their synchronous movements—surround the organ 22 to be removed, and to place the tubular casing 12 around the organ 22 during this. For this purpose, the gripping arms 30 consist of a multitude of elements that are pivotally interconnected, as is shown schematically in FIG. 3, and/or the gripping arms 30 are embodied flexibly and elastic transverse to their longitudinal extent. The outward spreading motion can for example be generated by micro-actuators and/or springs and/or a special interaction of shape and elasticity, which are not shown in the figures.

The relative movement between the gripping arms 30 and the inner tube 6 can even be assisted by intending that during the spreading movement of the gripping arms 30 the inner tube 6 is subjected to an opposing movement back in the direction towards the sleeve 8 and thus commences to be retracted into the sleeve 8 and the outer tube 4, as is indicated by arrow B in FIG. 3. This results in the organ 22 being quasi-delivered between the spread gripping arms 30.

During this sequence of motion, the originally spread-apart gripping arms 30 enclose the organ 22 to be removed by moving their proximal ends 30a towards each other. This movement, being the opposite to the spreading movement, can for example be effected by the above-mentioned micro-actuators, which are not shown in the figures, or through a combined effect of special shape design and elasticity.

Figure 4:
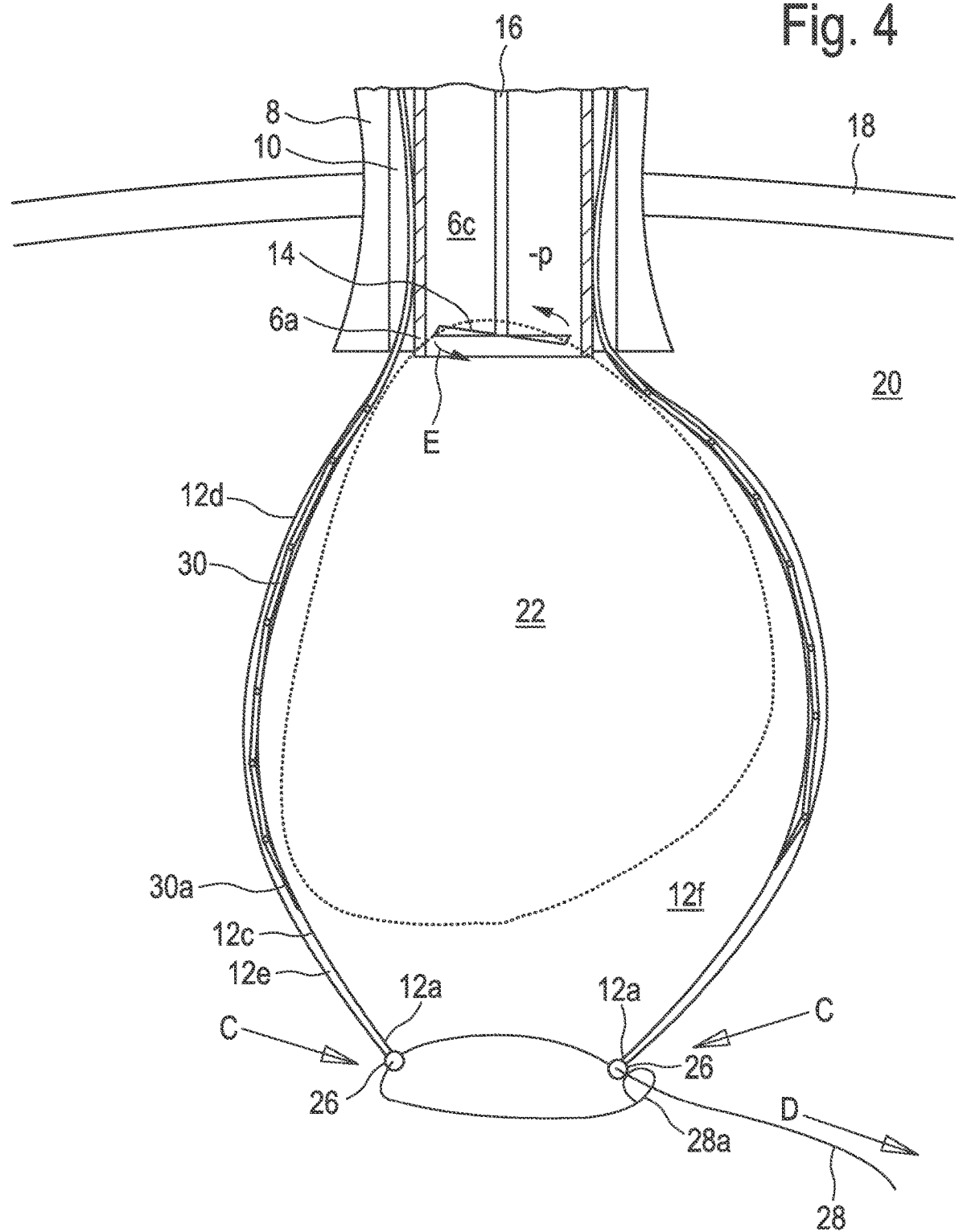
FIG. 4 shows in a schematic longitudinal sectional view an enlarged partial view of the device of FIG. 1 in a fourth operating state.

As the movement of the proximal ends 30a of respective opposing gripping arms 30 along the direction or arrow C progresses, which is shown in FIG. 4, the gripping arms 30 enclose the organ 22 to be removed, so that this movement can also be referred to as a closing movement. This closing movement results in the gripping arms 30 placing the tubular casing 12 around the organ 22 to be removed, which on account of the suction effect in the cavity 6c of the inner tube, is still attached to the proximal end 6a of the inner tube 6. In this fourth operating state, as it is shown in FIG. 4, the inner tube 6 is again retracted into the sleeve 6 to such a degree that the proximal end 6a of the inner tube 6 is situated approximately at the level of the proximal end 8a of the sleeve 8. As mentioned above, the upward movement of the inner tube 4 with the attached organ 22 promotes the closing movement of the gripping arms and the resulting enclosing of the organ 22 by the tubular casing 12.

Figure 5:
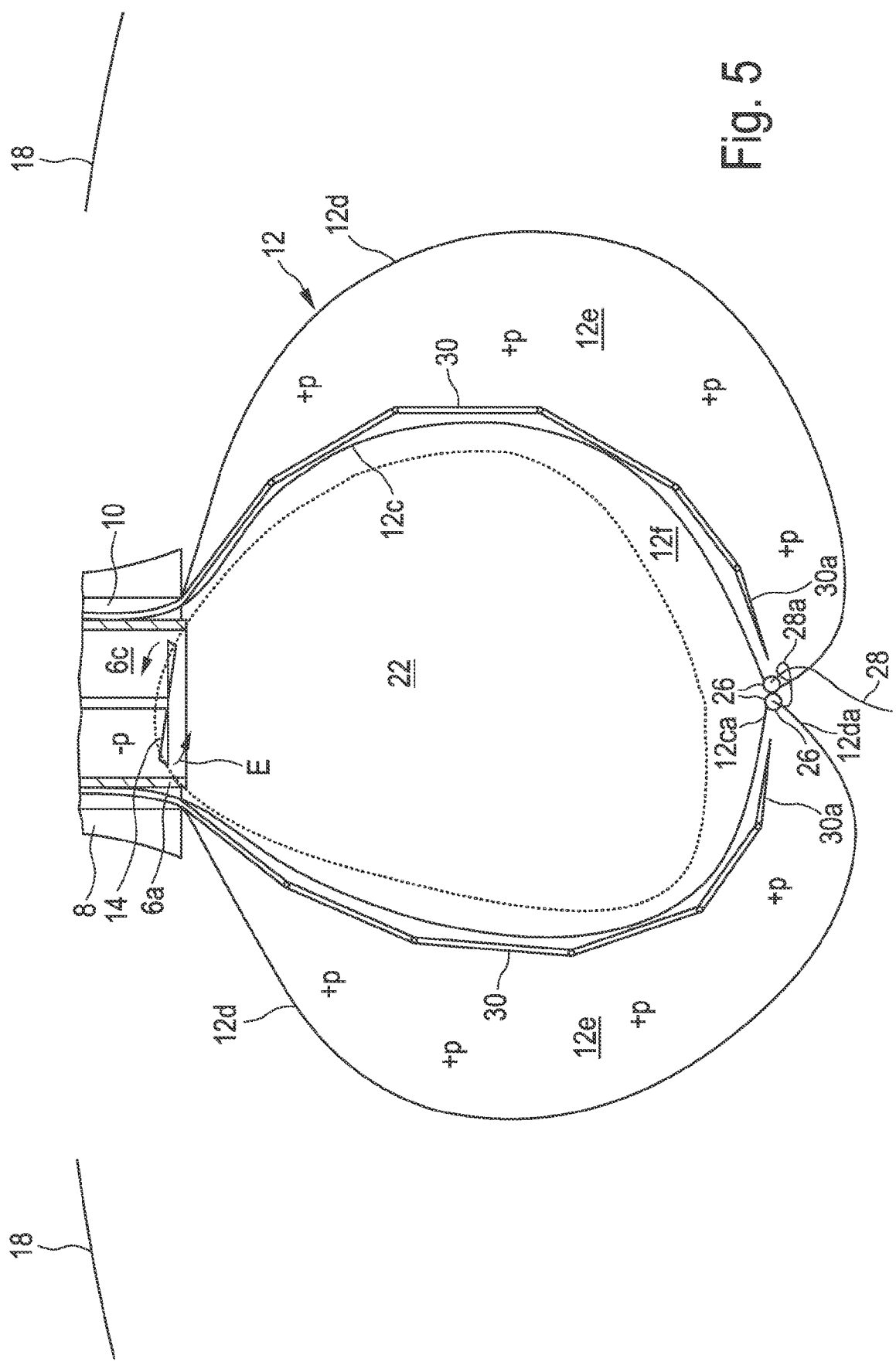
FIG. 5 shows in a schematic longitudinal sectional view an enlarged partial view of the device of FIG. 1 in a fifth operating state, now with the organ to be removed completely enclosed by a tubular casing.

Contrary to the illustrations of FIGS. 3 and 4, during the sequences of movement described using FIGS. 3 and 4, the gripping arms 30 with their proximal end 30a usually substantially are in contact with the inner side of the closed proximal end 12a of the tubular casing 12 embodied as a double casing, which also facilitates guiding the tubular casing 12 in the area of its proximal end 12a by means of the gripping arms 30, which by the way is also evident in FIG. 5.

In the third operating state of the device 2 according to FIG. 3 and also in the fourth operating state of the device 2 according to FIG. 4, and the corresponding sequences of movement of the gripping arms 30 described above, the thread 28 guided through the loop 28a and the eyelets 26 arranged at the proximal end 12a of the tubular casing 12 remains in a very loose state in order to not impede the described movement sequences and in particular the enclosure of the organ 22 by the tubular casing 12.

The last part of the movement of the proximal ends 30a of the gripping arms 30 towards each other in the direction of arrow C now is assisted or even exclusively taken over by the thread 28, by subjecting the thread 28 to a tensile movement along the direction indicated by the arrow D shown in FIG. 4. As a result of this, the tubular casing 12 can be closed at its proximal end 12a as is indicated in FIG. 5, which shows a fifth operating state of the device 2. Thus the tubular casing 12 now forms a closed cavity 12f that is enclosed by its inner casing 12c and contains the organ 22 to be removed. In other words, the tubular casing 12 now has the shape of a pouch that can accommodate the organ 22 to be removed.

Furthermore, in the fifth operating state of the device 2 shown in FIG. 5, pressurized air has been injected through the interspace 10 between the outer tube 4 and the sleeve 8 on the one hand and the inner tube 6 on the other hand (FIG. 1) and also has been injected into the interspace 12e, which adjoins the interspace 10 and is located between the inner casing 12c and the outer casing 12, for which purpose a pressurized air source (not shown in the figures) is connected to the interspace 10 in the area of the distal end 4b of the outer tube 4. As a result of this, the interspace 12e between the inner casing 12c and the outer casing 12d is inflated, whereby the overpressure prevalent in this interspace 12e is indicated by the label "+p" in FIGS. 5 and 6. This overpressure results in pressure on the organ 22 to be removed via the inner casing 12c on the one hand and in the inflation of the outer casing 12d on the other.

Figure 6:
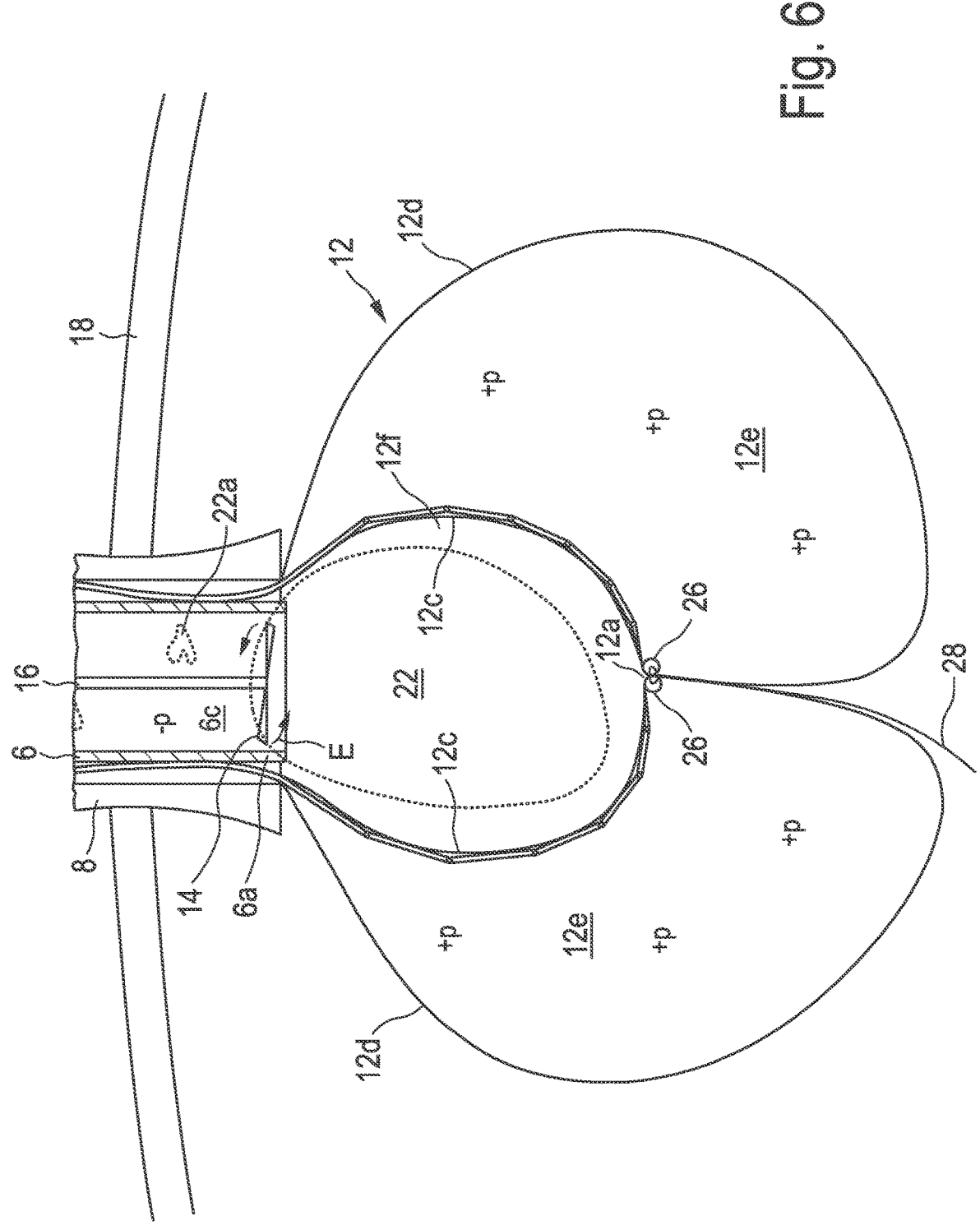
FIG. 6 shows in a schematic longitudinal sectional view an enlarged partial view of the device of FIG. 1 in a sixth operating state, with the organ to be removed completely enclosed by the tubular casing.

Due to the underpressure prevalent in the cavity 6c of the inner tube 6, the organ 22 to be disposed of not only is suctioned to the proximal end 6a of the inner tube 6, but also is drawn inside the latter and during this reaches the effective range of the rotary blade 14 rotating in the direction of the arrow E. Due to the additional pressurization via the inner casing 12c on account of the overpressure prevalent upstream in the interspace 12e, the organ 22 to be removed is pressed more strongly into the proximal end 6a of the inner tube 6, while the organ 22 simultaneously is subjected to compression. This effect is enhanced by the organ 22 being comminuted into individual pieces by the rotary blade 14, which then are easier to suck up through the inner tube 6. This sixth operating state of the device 2 is shown in FIG. 6, which for exemplary purposes also shows a piece 22a of the organ 22 in the cavity 6c of the inner tube 6 that has been cut from the organ 22 by the rotary blade 14.

Figure 7:
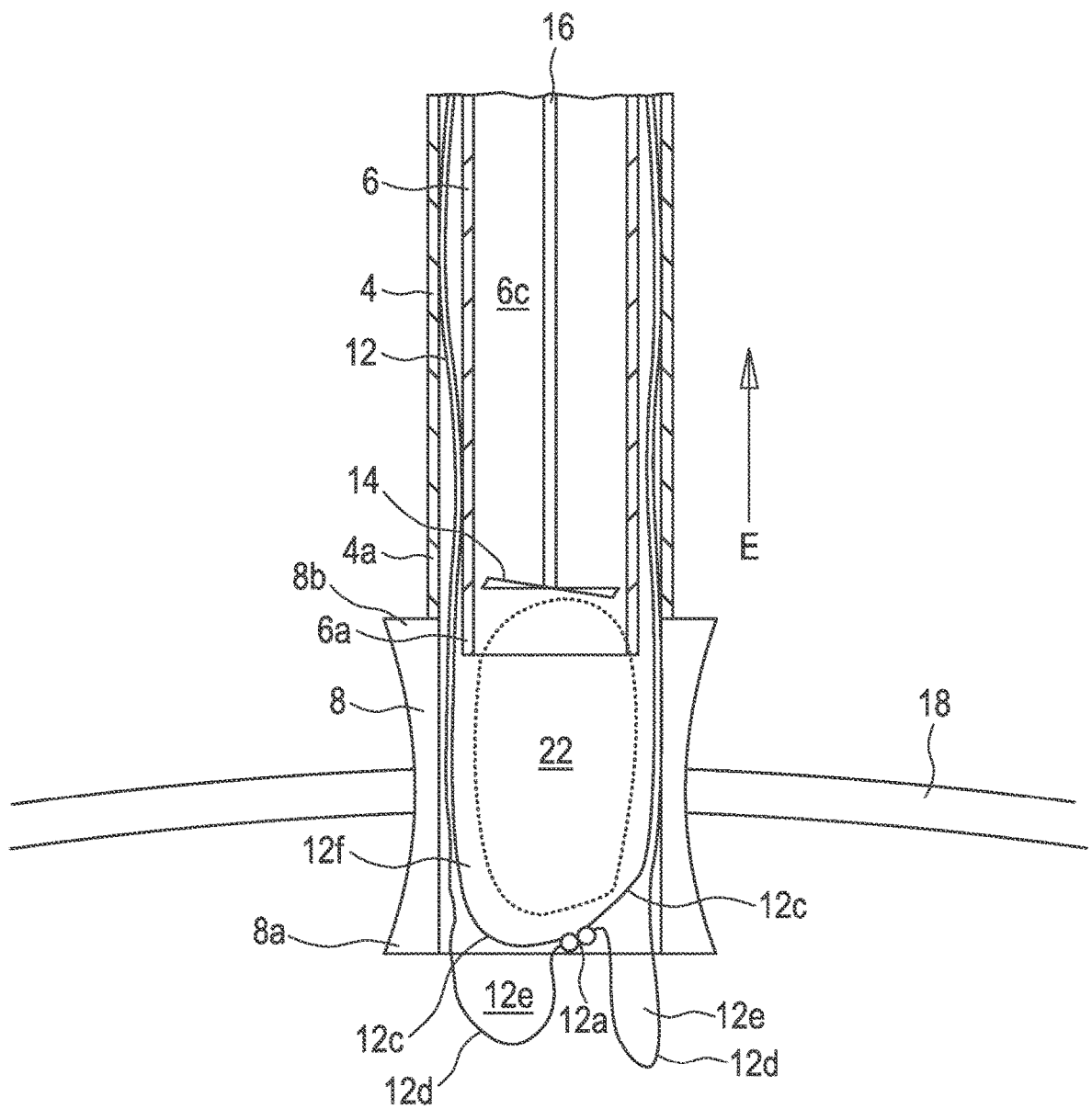
FIG. 7 shows in a schematic longitudinal sectional view an enlarged partial view of the device of FIG. 1 in a seventh operating state, with the organ substantially removed from the body.

When the organ 22 to be removed has been compressed by the combined effect of the suction pressure at the proximal end 6a of the inner tube 6, the over pressure exerted on the organ 22 via the inner casing 12c of the tubular casing 12, and the rotary blade 14, to a width that is at least less than the inner diameter of the sleeve 8 and of the adjacent outer tube 4, the remaining, thusly contracted organ 22 can be removed from the body 20 as a single piece in one further operational step. The corresponding seventh operating state of the device 2 is shown in FIG. 7. In this operating state, the overpressure in the interspace 12e between the inner casing 12c and the outer casing 12 of the double-walled tubular casing 12 is switched off or eliminated, and this interspace 12e is vented via the interspace 10 between the outer tube 4 and the sleeve on the one side and the inner tube 6 on the other side in the area of the distal end 4b of the outer tube 4, as a result of which both the inner casing 12c as well as the outer casing 12 enter into a relaxed state. While the inner casing 12c continues to perform the function of a pouch accommodating the remaining organ 22, and thus continues to be loaded by the weight of the remaining organ 22, the outer casing 12d now is in a completely unloaded and thus loose and flaccid state, as is indicated in FIG. 7.

On principle it can be envisioned that the organ 22 even in its contracted state, as it is shown in FIG. 7, can be further comminuted by means of the rotary blade 14, and that the individual parts are subsequently suctioned off through the cavity 6c of the inner tube 6. However, in the seventh operating state shown in FIG. 7, one foregoes a further comminuting by means of the rotary blade 14, but instead the inner tube 6 with the remaining organ 22 still secured at its proximal end 6a now is moved along the direction of arrow E shown in FIG. 7, namely completely out of the body 20 and also out of the sleeve 8 into the outer tube. Since now further comminuting of the organ by the rotary blade 14 is no longer required, it is intended that during this retraction movement of the inner tube 6 the rotary shaft 16 holding the rotary blade 14 simultaneously is moved out of the sleeve 8 in the direction towards the distal end 4b of the outer tube 4, whereby the movement of the rotary shaft 16 and of the inner tube 6 along the arrow E may also take place synchronously. Moreover, during this movement, the rotary blade 14 is no longer active, so that the rotary shaft 16 is stationary along its rotational direction, i.e. is no longer subject to rotation. Consequently, in this embodiment, the comminuting device comprising the rotary blade 14 and the rotary shaft 16 is designed so that it is moveably arranged between a lower operating position, in which the rotary blade 14 is situated in the area of the proximal end 8a of the sleeve 8 and in this is still located inside the inner tube 6, as is shown in FIGS. 1 to 6, and an upper rest position, separated from the sleeve 8 in the direction towards the distal end 4b of the outer tube, whereby it preferably is still situated within the inner tube 6; the associated support and guide elements and a possibly required drive are not shown in the figures.

FIG. 8 shows the device 2 in an eighth operating state, in which the outer tube 4 with the now again retrieved inner tube 6 and the organ 22 now contained in the tubular casing 12 has been extracted from the sleeve 8 that is still remaining in the skin 18. Subsequently, the residual organ 22 is removed from the device 2 and is disposed in the same manner as the individual components 22a cut off earlier (FIG. 6).

Figure 9:
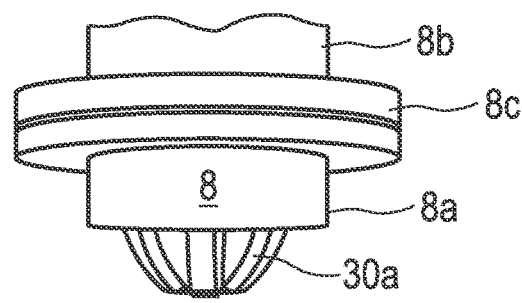
FIG. 9 shows schematically in an enlarged partial perspective view a sleeve and the proximal ends of gripping arms forming at least a part of a handling device, in a still closed position as part of a device to remove organs from the human or animal body in accordance with a second preferred embodiment.

FIG. 9 shows schematically in an enlarged, partial perspective view only the sleeve 8 and the proximal ends 30a of the gripping arms in a still closed state. In contrast to the illustrations in FIGS. 1 to 8, the illustration of FIG. 9 shows the sleeve 8 still equipped with a circumferential flange 8c, which during the insertion of the sleeve 8 into the skin 18 of the body 20 comes to rest on the skin 18, and in this manner simply but more effectively facilitates securing the device 2 in position on the skin 18.

Figure 10:
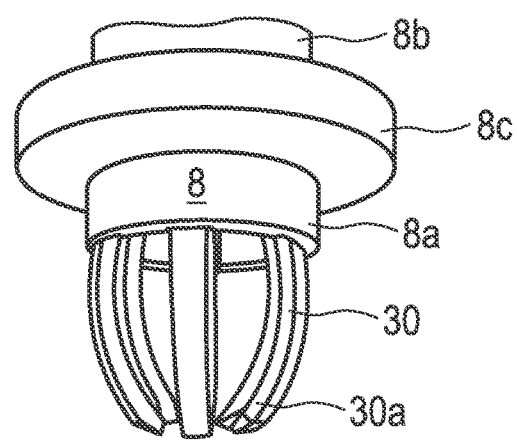
FIG. 10 shows substantially the same view as FIG. 9, but with the gripping arms in a slightly opened state.

FIG. 10 shows substantially the same view as FIG. 9, whereby in contrast to FIG. 9, where the gripping arms are not only shown with their proximal ends 30a in a closed state, but also in a position, where they are substantially completely retracted in the sleeve 8, the gripping arms 30 now are further extended towards the organ to be removed, which is not illustrated in FIG. 10, and are already slightly opened.

Figure 11:
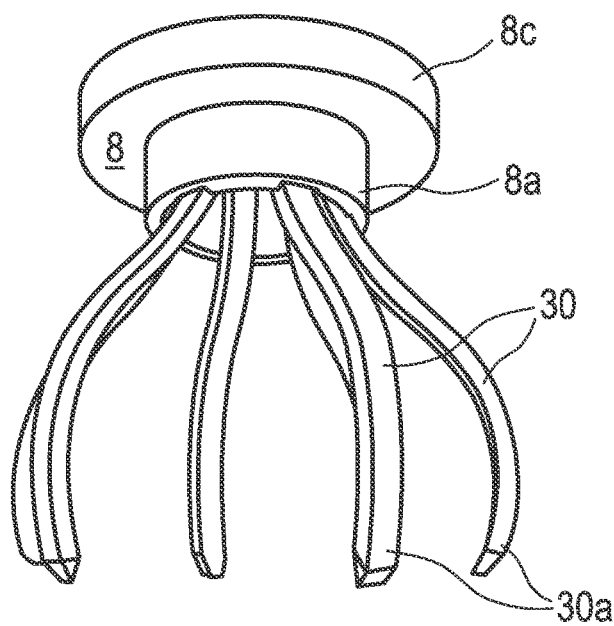
FIG. 11 shows substantially the same view as FIG. 9, but with the gripping arms in a completely spread, i.e. opened state.

FIG. 11 shows substantially the same view as FIG. 9, but with the gripping arms 30 now substantially completely spread, whereby this approximately corresponds to the third operating state of the device 2 shown in FIG. 3.

FIG. 12 shows in a schematic perspective view a unit of inner tube 6, sleeve 8, and gripping arms 30 as part of a device for removing organs from the human or animal body in accordance to a further preferred embodiment. For reasons of clarity, of the inner tube 6 is only shown its section, which is adjacent to its proximal end 6a, projects from the sleeve 8 into the body 20, and thus is exposed. Furthermore, the gripping arms 30 form part of a handling device, the remainder of which is not shown. As in the embodiment shown in FIGS. 9 to 11, the sleeve 8 shown in the embodiment in FIG. 12 also comprises a circumferential flange 8c.

Furthermore, in the embodiment of FIG. 12, the gripping arms 30 at their distal ends 30b are connected to each other via an annular connecting element 32, as a result of which the gripping elements 30 can be moved jointly and synchronously along the longitudinal direction of the inner tube 6. The annular connecting element 32 consequently also is a component of the handling device (the remainder of which is not shown) and preferably is coupled to a suitable drive, which constitutes a further component of the mentioned handling device but is not shown in the figures.

Furthermore, in the embodiment of FIG. 12, the exterior side of the inner tube 6 is provided with guide grooves 34, which extend in the former's longitudinal direction, and in which the gripping arms 30 are accommodated moveable along the guide grooves' longitudinal direction.

Finally, the gripping arms 30 are arranged between the inner side of the sleeve 8 and the exterior side of the inner tube 6 and substantially are in contact with the inner side of the sleeve 8 on the one hand and the exterior side of the inner tube 6 on the other.

As is further evident in FIG. 12, in which the gripping arms 30 are shown in a relaxed state, the proximal ends 30a of respective opposing gripping arms 30 are separated by a distance that is less than the diameter of the inner tube 6. Furthermore, according to FIG. 12, the gripping arms 30 comprise between their proximal and distal ends 30a, 30b a central section, which relative to the inner tube is curved outward, so that at least at the position that is the furthest outward along their radial extent, the distance of the central section from the respective opposing gripping arms 30 is greater than the diameter of the inner tube 6.

Of the gripping arms 30 shown in FIG. 12, a single gripping arm 30 is shown in FIG. 13 in a lateral view, so that the extent and the shape of the gripping arm 30 are easily discernable in FIG. 13. In accordance with the embodiment example illustrated in FIG. 13, the gripping arm 30 comprises—adjacent to its proximal end 30a—a first outwardly curved section 30c and adjacent to its distal end 30b, a second outwardly curved section 30d, whereby the two outwardly curved sections 30c, 30d are connected via the central section 30e, which in turn is embodied with an arched shape. As is further evident in FIG. 13, the proximal and distal ends 30a, 30b are aligned approximately flush relative to each other. Finally, the gripping arm 30 consists of an elastic material, preferably plastic.

In the embodiment example illustrated in FIGS. 12 and 13, in the retracted final position of the handling device, the gripping arms 30 in their so-called initial position are forcibly delivered into a substantially completely stretched state within the interspace 10 between the outer tube 4 and the sleeve 8 on the one hand and the inner tube 6 on the other hand (FIG. 1), and thus are substantially completely extended, since the radial aperture width of the interspace 10 is only insignificantly greater than the radial thickness of the gripping arms 30, and since there is no substantial clearance in the interspace 10 between the exterior side of the inner tube 6 on the one hand and the inner side of the outer tube 4 and the sleeve 8 on the other hand. Consequently one can also see this state as a forced constraint, which is a result of the mentioned configuration and doesn't leave the gripping arms 30 with any other choice but to assume a substantially completely extended shape. Once the handling device is moved into the body 20 towards the organ 22 to be removed (FIG. 1) and consequently towards its proximal final position, the shape of the first outwardly curved section 30c at first causes the gripping arms to spread apart in the region of their proximal end 30a. This spreading movement continues until the central section 30e of the gripping arms 30 emerges from the sleeve 8 with its portion that is situated the furthest radially outward, so that at this moment the gripping arms 30 assume a similarly spread position, as is shown in FIG. 11. During the continued movement out of the sleeve 8, the shape of the gripping arms 30 between the central section 30e and the second curved section 30d in the direction of the distal end 30b causes a renewed closing of the gripping arms 30 at their proximal ends 30a, in particular no later than when the curved central section 30e of the gripping arms 30 is exposed outside the sleeve 8 and thus the gripping arms 30 are no longer subject to any constraints imposed by the sleeve 8; then the gripping arms 30 will assume approximately the position that is shown in FIG. 12.

FIG. 14 shows in a schematic perspective representation a part of the handling device with gripping arms 30 as part of a device for removing organs from the human or animal body, in accordance with a further preferred embodiment. As is evident in FIG. 14a, the embodiment shown here differs from the embodiment of FIG. 12 in that a so-called spreading element 36 is arranged in each guide groove 34 in the area of the proximal, end 6a of the inner tube 6. The spreading elements 36 have a triangular shape and on their outside possess a guide surface 36a, which rises from the bottom of the associated guide groove 34 in the direction towards the proximal end 6a of the inner tube 6, so that the radial distance of the guide surface 36a of the spreading elements 36 from the central axis of the inner tube 6 at the proximal end 6a of the inner tube 6 is greater than the radius of the inner tube 6. During the movement of the gripping arms 30 out of the sleeve 8 and in this along the guide grooves 34, the gripping arms 30 with their proximal end 30a initially come into bearing contact with the guide surfaces 36a of the spreading elements 36 and during the continuing movement are pushed outward along the guide surface 36a of the spreading elements 36, so that consequently the spreading elements 36 act like a wedge or cone in spreading apart the abutting gripping arms 30.

As is further evident in FIG. 14, the spreading elements 36 are arranged spaced apart at a distance corresponding to the separation of the gripping arms 36 and each gripping arm 30 is associated with one spreading element. To facilitate detaching the gripping arms 30 from the spreading elements 36, the inner tube 6 on the one hand and/or the gripping arms 30 on the other hand can be made to impinge upon each other by a relative movement, in order to pass the gripping arms 30, which up to now were bearing upon the spreading elements, to a lateral position next to the spreading elements 36. Consequently, a lateral displacement of the inner tube 6 relative to the gripping arms 30, or a lateral displacement of the gripping arms 30 by applying a rotating movement to the ring 32 that connects the gripping arms 30 at their distal end 30b, or a corresponding joint lateral displacement of the inner tube 6 and the gripping arms 30 relative to each other, causes the gripping arms 30 to slide off the spreading elements and thus causes the gripping 30 arms to close. As is shown in detail in particular in FIG. 14b, the spreading elements 36 may be embodied with a width less than that of the guide grooves 34 and may be arranged laterally within the guide grooves 34, so that after the gripping arms 30 slide off the spreading elements 36, the gripping arms 30 can be accepted by the guide grooves 34 again; however, for this it is necessary that the width of the gripping arms 30 can not be greater than the remaining inner width of the guide grooves 34 in the region of the spreading elements 36.

The invention claimed is:

1. A device for removing organs from a human or animal body, comprising:
   a tube that comprises a proximal end and a distal end and is intended to be partially inserted into the body with its proximal end, whereby the distal end of the tube can be connected to a suction air source and the proximal end of the tube is embodied for a suction engagement with the organ to be removed;
   a tubular casing, which at least sectionally encompasses the tube, and which possesses a proximal end and a distal end, by which it is attached to the tube;
   a handling device, which is arranged at the tube and is embodied to open or extend the tubular casing at its proximal end and to guide or place it around the organ;
   a closing device, that is embodied to close the proximal end of the tubular casing, and
   a comminuting device that is provided within the tube in the area of its proximal end.

2. The device of claim 1, wherein the handling device is moveable along the longitudinal direction of the tube between an extended proximal end position and a retracted distal end position.

3. The device of claim 2, in which the handling device is arranged relative to the tube moveable in the latter's transverse direction.

4. The device of claim 2, in which the handling device comprises spreading elements, which are embodied to spread the gripping arms at least temporarily apart from each other during the movement of the handling device into its proximal final position.

5. The device of claim 4, in which the spreading elements are arranged at the tube in the area of its proximal end, and posses a guide surface, which rises from the outer surface of the tube towards its proximal end, and to which the gripping arms may be brought in contact with.

6. The device of claim 5, in which the spreading elements are arranged in the guide grooves and their guide surface rises from the bottom of the guide grooves.

7. The device of claim 5, in which the spreading elements are arranged some distance apart from each other, each gripping arm is associated with one spreading element, and for the purpose of releasing the gripping arms from the spreading elements, the tube on the one side and/or the gripping arms on the other side can be made to impinge upon each other in a relative movement, in order to position the gripping arms into a lateral position next to the spreading elements.

8. The device of claim 1, in which the handling device comprises gripping arms, which oppose each other, and each of which possesses a proximal free end and a distal end, and which for the purpose of releasably gripping the tubular casing are embodied in the area of the latter's proximal end.

9. The device of claim 8, in which the gripping arms possess, in the area of the proximal end, securing means, which are embodied to releasably secure in position the tubular casing, with its proximal end, at the gripping arms.

10. The device of claim 8, in which the gripping arms are oriented along the longitudinal direction of the tube.

11. The device of claim 8, in which the gripping arms are elastic at an angle, approximately transversely, to the longitudinal extent of the tube.

12. The device of claim 11, in which in a relaxed state of the gripping arms the proximal ends of respective opposing gripping arms are separated by a distance that is less than the diameter of the tube, and a central section of the gripping arms that is located between the proximal and the distal ends is curved outward with respect to the tube, so that the distance between the central sections of respective opposing gripping arms is greater than the distance between the proximal ends of said gripping arms.

13. The device of claim 12, in which the distance between the central sections of respective opposite gripping arms is greater than the diameter of the tube.

14. The device of claim 8, in which the gripping arms are embodied to be longer than the tube.

15. The device of claim 8, in which the outer surface of the tube is provided with guide grooves extending along the former's longitudinal direction, in which the gripping arms are accommodated moveably along the groove's longitudinal direction, and the arrangement is designed so that in the proximal final position of the handling device, the gripping arms with a section adjoining to their proximal end protrude beyond the proximal end of the tube, and consequently are exposed.

16. The device of claim 8, in which the gripping arms are connected to each other in the area of their distal ends.

17. The device of claim 16, with an annular element, to which the gripping arms are attached to by their distal end.

18. The device of claim 8, in which the closing device comprises closing means, which are provided at the gripping arms, preferably at their free or proximal ends.

19. The device of claim 1, in which the closing device is provided at the handling device.

20. The device of claim 1, in which the closing device at the proximal end of the tubular casing comprises eyes or eyelets, and at least one thread or wire that can be threaded through the eyes or eyelets.

21. The device of at least one of claim 1, in which the comminuting device comprises at least one rotatably supported cutting blade.

22. The device of claim 1, further comprising a sleeve to be arranged on the surface of the body or to be inserted into the surface of the body, whereby the tube extends through the sleeve and is moveable relative to the sleeve.

23. The device of claim 22, in which the gripping arms are arranged between the inner side of the sleeve and the outer side of the tube, and are in contact with the inner side of the sleeve and the outer side of the tube.

24. The device of claim 22, in which the inner side of the sleeve is provided with guide grooves, which extend along the direction of movement of the handling device, and in which the gripping arms are arranged moveable along the longitudinal direction of said guide grooves, and the arrangement is designed so that in the proximal final position of the handling device, the gripping arms with a section adjoining their proximal end project beyond the proximal end of the tube and consequently are exposed.

25. The device of claim 22, in which the sleeve possesses a flange-like rim to bear upon the surface of the body.

26. The device of claim 1, in which the tubular casing is embodied as a double casing with an inner casing and an outer casing that surrounds the inner casing at a distance, thus forming an interspace, and a pressurized air source can be connected to the interspace formed between the inner casing and the outer casing.

27. The device of claim 26, in which the closing device is embodied to close the proximal end of the inner casing and to close the proximal end of the outer casing.

28. The device of claim 26 in which the closing device is embodied to jointly close the proximal ends of the inner casing and the outer casing.

29. The device of one of claim 26, in which the handling device is at least sectionally arranged in the interspace formed between the inner casing and the outer casing.

30. The device of one of claim 26, in which the inner casing is connected to the outer casing in a sealing manner at the proximal end of the tubular casing.

31. The device of claim 26, in which the inner casing is mounted on the inner tube and the outer casing is mounted on the outer tube, and the pressurized air source can be connected to the interspace formed between the interior tube and the exterior tube.

32. The device of claim 1, in which the tube is embodied as an inner tube, which is surrounded by an outer tube at a distance which creates an interspace, the inner tube is arranged moveable relative to the outer tube and in this a section adjacent to its proximal end can be extracted out of the proximal end of the outer tube, the tubular casing prior to its use is arranged substantially in the interspace between the inner tube and the outer tube and can be exposed by extracting the inner tube from the outer tube, and the comminuting device is provided within the inner tube, in the region of its proximal end.

33. The device of claim 32, in which a sleeve is arranged at the proximal end of the outer tube or is formed by the outer tube.

34. The device of claim 33, in which the handling device is arranged and embodied on the exterior side of the inner tube.

35. The device of claim 32, in which the handling device is arranged and embodied at the exterior tube.

36. The device of claim 32, in which the tubular casing is attached to the inner tube by its distal end.

37. The device of one of claim 32, in which the inner tube is embodied in a fashion so that during its extraction from the outer tube it takes along and thus substantially exposes the tubular casing.

* * * * *